United States Patent [19]

Seshimoto et al.

[11] Patent Number: 4,842,712
[45] Date of Patent: Jun. 27, 1989

[54] DEVICE FOR MEASURING ION ACTIVITY

[75] Inventors: Osamu Seshimoto; Masaaki Terashima; Yoshio Saito, all of Asaka, Japan

[73] Assignee: Fuji Photo Film Co., Ltd., Kanagawa, Japan

[21] Appl. No.: 9,470

[22] Filed: Feb. 2, 1987

[30] Foreign Application Priority Data

Jan. 31, 1986 [JP] Japan .................. 61-19950
Apr. 11, 1986 [JP] Japan .................. 61-83676

[51] Int. Cl.⁴ ............................ G01N 27/46
[52] U.S. Cl. ................... 204/416; 204/403; 204/418; 204/435
[58] Field of Search ............... 204/416–419, 204/435, 182.7

[56] References Cited

U.S. PATENT DOCUMENTS

| | | | |
|---|---|---|---|
| 2,962,426 | 11/1960 | Sharpsteen | 204/182.7 |
| 3,000,804 | 9/1961 | Cahoon et al. | 204/435 |
| 3,103,480 | 9/1963 | Watanabe et al. | 204/416 |
| 3,432,424 | 3/1969 | Zee | 204/182.7 |
| 3,461,055 | 8/1969 | Staunton | 204/435 |
| 3,575,834 | 4/1971 | Hoole et al. | 204/435 |
| 4,397,908 | 8/1983 | Phillips . | |
| 4,437,970 | 3/1984 | Kitajima et al. | 204/435 |
| 4,684,445 | 8/1987 | Seshimoto et al. | 204/412 |

FOREIGN PATENT DOCUMENTS 0095946 12/1983 European Pat. Off. .
0164133 12/1985 European Pat. Off. .
0207530 1/1987 European Pat. Off. .

Primary Examiner—T. Tung
Attorney, Agent, or Firm—Jules E. Goldberg

[57] ABSTRACT

In a device for measuring ion activity in a liquid sample such as a body fluid comprising at least one pair of ion-selective electrodes selectively responsive to a specific ion, a porous liquid distributing member for feeding a liquid sample to one electrode of the pair of electrodes, a porous liquid distributing member for feeding a reference liquid to another electrode of the pair of electrodes and a porous bridge for electrically connecting both liquids to each other, the improvement wherein the liquid distributing members are made of a nonwoven fabric composed of cellulosic long fibers.

4 Claims, 4 Drawing Sheets

DEVICE FOR MEASURING ION ACTIVITY

BACKGROUND OF THE INVENTION

1. Field of the Invention

The present invention relates to a device for measuring ion activity for the quantitative analysis of a specific ion activity (or ion concentration) contained in an aqueous liquid, particularly a body fluid such as blood, urine or saliva by utilizing potentiometry.

2. Description of Prior Art

There have been known methods for measuring specific ion activity contained in a liquid sample (e.g., tap water, river water, sewage or industrial drainage) or a body fluid (e.g., blood, urine or saliva) by using an ion activity mesuring device in the form of a sheet.

In these methods, a reference liquid and a liquid sample are spotted onto the surface of the ion-selective membrane of each of a pair of ion-selective electrode sheets which are electrically insulated from each other, and then a potential difference between the ion-selective electrodes is measured under such conditions that both liquids are electrically connected to each other through a bridge, to thereby determine the ion activity of the liquid sample.

Examples of such ion activity measuring devices employable in these methods, are described, for instance, in Japanese Patent Provisional Publication Nos. 52(1977)-142586, 56(1981)-6148 and 58(1983)-211648.

In these devices, a pair of ion-selective electrode sheets are arranged in such a manner that ion-selective membranes are positioned on the upper side, and on the ion-selective membranes are provided with liquid receiving openings (openings for introducing a reference liquid and a liquid sample). In practically determining the ion activity by the use of these devices, the reference liquid and the liquid sample are spotted on the ion-selective membranes through the liquid receiving openings by using a pipet, etc. and a potential difference between both ion-selective electrodes is measured to thereby determine ion activity. There is also known a device comprising plural pairs of ion-selective electrodes, which can determine ion activity of plural kinds of ions by only once-spotting of a reference liquid and a liquid sample thereonto. Such a device is disclosed in Japanese Patent Provisional Publication No. 58(1983)-211648.

Though the above-described method using plural pairs of the ion-selective electrodes for determining ion activity of several kinds of ions simultaneously is simple and advantageous, it has been found that the method has the following disadvantages.

When a bandage, a flax net, a lawn, a silk gauze or a filter paper is used s a porous liquid distributing member, said method has a problem in that in the measurement of ion activity, particularly potassium ion activity in whole blood, diluted whole blood solution or a blood sample containing blood cells (particularly, erythrocyte), the blood sample suffers hemolysis in the ion activity measuring device and as a result, the measured value of potassium ion activity is often deviated from true potassium ion activity in the blood sample and does not coincide with potassium ion activity in plasma or serum obtained by removing blood cells from the same blood sample.

When a gauze is used as a porous liquid distributing member, hemolysis is inhibited to a large extent, but it is easily deformed and has much difficulty in cutting it into a given length. When a cloth composed of a synthetic polymer fiber such as a polyester fiber is used, whole blood hardly suffers hemolysis, but the spreading of the liquid is very slow.

Therefore, these materials are not satisfactorily employable as a liquid distributing member for the abovedescribed ion activity measuring device which enables ion activity of several kinds of ions to be simultaneously measured by only one device.

SUMMARY OF THE INVENTION

It is an object of the present invention to provide an ion activity measuring device which is freed from the problem of an error in measurement caused by hemolysis in the measurement of potassium ion activity in a blood sample containing blood cells such as whole blood.

It is another object of the invention to provide an ion activity measuring device which enables ion activity of plural kinds of ions in a blood sample containing blood cells such as whole blood to be measured almost simultaneously by only one device and is freed from the problem of an error in measurement caused by hemolysis in the measurement of potassium ion activity.

There is provided by the present invention an improvement in a device for measuring ion activityin a liquid sample comprising at least one pair of ion-selective electrodes selectively responsive to a specific ion, a porous liquid distributing member for feeding a liquid sample to one electrode of the pair of electrodes, a porous liquid distributing member for feeding a reference liquid to another electrode of the pair of electrodes and a porous bridge for electrically connecting both liquids to each other, wherein said liquid distributing members are made of a nonwoven fabric composed of cellulosic long fibers.

The device for measuring ion activity of the invention preferably has at least two pairs of ion-selective electrodes.

DETAILED DESCRIPTION OF THE INVENTION

As the nonwoven fabric composed of the cellulosic long fibers, cellulosic spun bonded nonwoven fabrics containing essentially no binder are preferred, and those composed of long fibers prepared from cotton linters are particularly preferred. For instance, there are preferred nonwoven fabrics prepared from a spinning solution of cotton linters dissolved in Schweizer's reagent by a spun bonding method. The thus-prepared nonwoven fabric generally absorbs blood in an amount of at least 10 times by weight as much as the weight of the fabric for a period of 3 seconds.

The thickness of the porous liquid distributing member used in the present invention is in the range of about 100 to about 400 μm.

The porous liquid distributing member used in the present invention may be in a form described in Japanese Patent Application No. 59(1984)-244200.

The ion activity measuring device of the invention may be in various forms.

Figure 1:
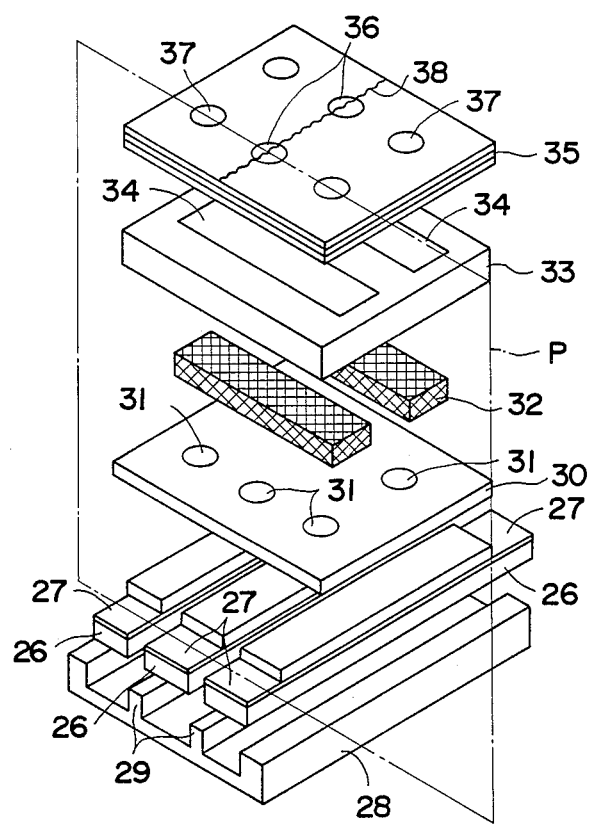
FIG. 1 is a perspective view showing an embodiment of the ion activity measuring device of the invention.

FIG. 1 shows an embodiment of the device according to the invention. Referring to FIG. 1, the device comprises pairs of sheet-form solid electrodes 26 provided with ion-selective layers on the upper surface thereof, electrically connecting terminals 27, a support frame 28 for receiving plural pairs of the solid electrodes, a water-impermeable sheet member 30 for covering the surfaces of the electrodes, liquid feeding holes 31 provided through the sheet member 30, porous members 32 for distributing liquids to the holes 31, two liquid reservoirs 34 for receiving a liquid sample and a reference liquid, respectively, a top lid 35 provided with spotting holes 36 and air-venting holes 37, and a porous bridge 38 composed of fibers for allowing the spotting holes 36 to communicate with each other.

The above-mentioned structure of ion-selective electrode is described in more detail in Japanese Patent Provisional Publication No. 58(1983)-2111648.

Other structures employable in the device of the invention are disclosed in Japanese Patent Provisional Publication Nos. 60(1985)-155960, 60(1985)-260843 or 60(1985)-260844.

Figure 2:
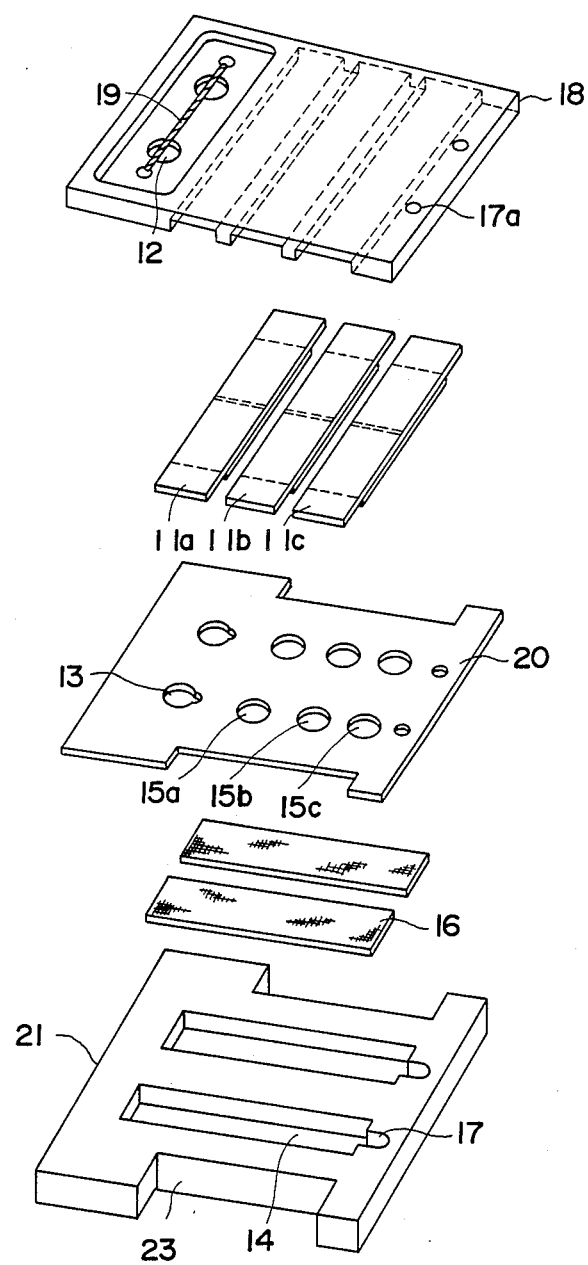
FIGS. 2 and 3 show members of other embodiment of the ion activity measuring device of the invention.

Further, as shown in FIG. 2, the device may comprise three pairs of ion-selective electrode sheets 11a, 11b and 11c, each electrodehaving an ion-sensitive layer on the under surface thereof and electrically connecting parts at both ends thereof; a top frame 18 provided with spotting holes 12 and air-venting holes 17, which is used for receiving plural pairs of the solid electrodes; a porous bridge 19 composed of fibers for allowing the spotting holes 12 to communicate with each other; a water-impermeable sheet member 20 provided in contact with the under surfaces of the ion-selective layers of the solid electrodes; liquid feed holes 13, 15a, 15b and 15c provided through the member 20; porous member 16 for distributing liquids to the holes 15a, 15b and 15c; and a bottom frame 21 for receiving the porous liquid distributing member within grooves 14. The number of each of the above members (including the liquid feed holes, the grooves, etc.) to be provided is such that there are provided a pair of individual members for the liquid sample and the reference liquid, excluding the pairs of the electrodes 11a, 11b and 11c; the top frame 18; the porous bridge 19; the water-impermeable sheet member 20; and the porous liquid distributing members 16.

Cutout parts 23 may be formed in plural pairs to correspond to the plural pairs of ion selective electrodes. Alternatively, a pair of cutout parts 23 may be formed on the both sides of the device to expose the electrically connecting parts of all ion selective electrodes.

The above-mentioned structure of ion-selective electrode is described in more detail in Japanese Patent Application No. 60(1985)-148564. If descired, the ion activity measuring device of the present invention may be one having a structure described in Japanese Patent Application Nos. 60(1985)-180358, 60(1985)-180359 or 60(1985)-180360.

Figure 3:
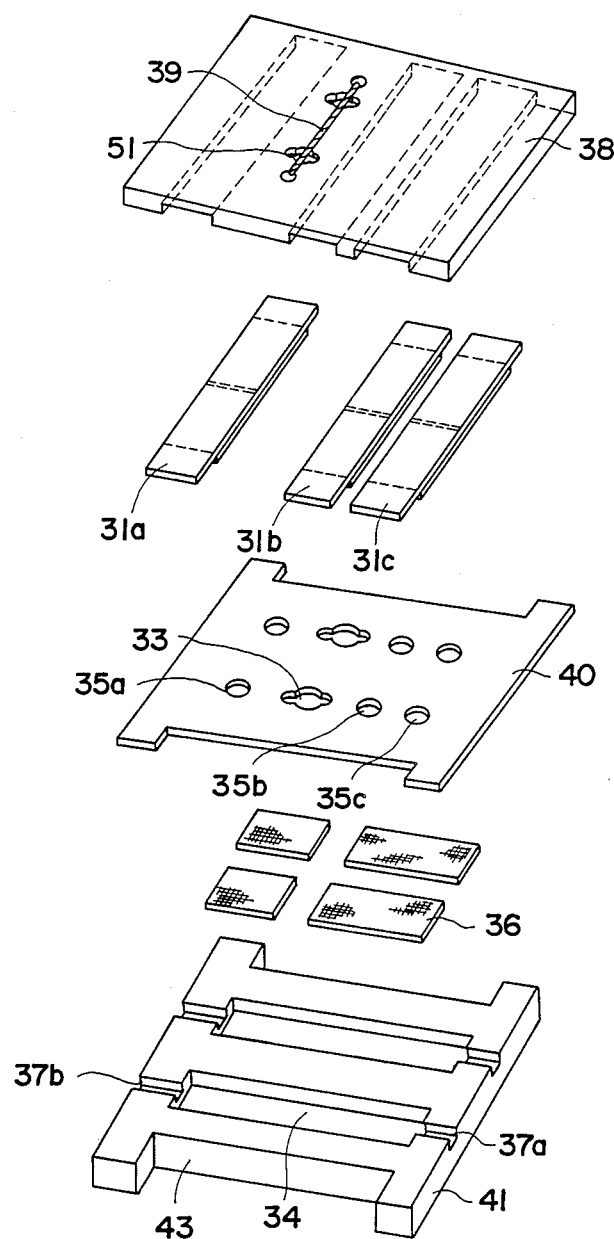

As shown in FIG. 3, the ion activity measuring device of the present invention may comprise three pairs of solid electrode sheets 31a, 31b and 31c provided with ion-selective layers on the under surfaces thereof; a top frame 38 which is provided with spotting holes 51 and used for receiving plural pairs of solid electrodes; a porous bridge 39 composed of a fiber for allowing the spotting holes to communicate with each other; a water-impermeable member 40 provided in contact with the under surfaces of the electrodes; liquid feed holes 33, 35a, 35b and 35c provided through the water-impermeable member 40; porous members 36 for distributing liquids to the liquid feed holes 35a, 35b and 35c; and a bottom frame 21 for receiving the porous liquid distributing member 36 composed of four parts in grooves 34. Said bottom frame 41 is provided with air-venting holes 37a and 37b. The porous bridge 39 may be passed through a line which is eccentrically out of the centers of the liquid feed holes. The bottom frame 41 may have cutout parts 43 on both sides to expose each of the electrically connecting parts of the electrodes If one electrode of the ion activity measuring device of the invention is directed for analysis of potassium ion. The preferred dimensions are as follows.

The distance from the area of the porous liquid distributing member for receiving a spotted liquid sample to the area where the liquid sample is brought about into contact with the electrode is not longer than 6 mm. The distance from one end of the distributing member or the area of the distributing member for receiving a spotted liquid sample to another end of the distributing member is not shorter than 8 mm, more preferably not shorter than 10 mm.

In the measurement of ion activity by using the above-described ion activity measuring device, a pair of the ion-selective electrodes among the three pairs of the ion-selective electrodes are used as sodium ion-selective electrodes, a pair of ion-selective electrodes among them are used as potassium ion-selective electrodes, and a pair of the ion-selective electrodes among them are used as chlorine ion-selective electrodes. When each of a reference liquid and a liquid sample is spotted on the spotting holes, each of the reference liquid and the liquid samples penetrates into the porous liquid distributing members, is passed through the liquid feed holes provided through the water-impermeable member and fed to the surface of each of the ion-selective electrodes. As a result, a potential difference and hence, the potential difference can be measured by a potentiometer through the electrical terminals provided at both ends of a pair of the ion-selective electrodes.

There can be used any of solid ion-selective electrodes described in Japanese Patent Provisional Publication Nos. 58-(1983)-211648, 60(1985)-237351, 60(1985)-237352, 61(1986)-7460, 61(1986)-7461 and 61(1986)-7462 and Japanese Patent Application No. 60(1985)-232306.

The ion-selective electrodes can be prepared by methods described in Japanese Patent Provisional Publication Nos. 58(1983)-102146, 58(1983)-156848 60(1985)-243555.

The following examples further illustrate the present invention.

EXAMPLE 1

Comparison between the extents of hemolysis

Each of distributing members (1.8 cm × 4 cm) made of the materials set forth in Table 1 was placed in a centrifuge tube for plasma separation. 500 μl of whole blood collected with heparin was added to each tube. After the tube was left to stand for one minute, the distributing member was taken out and the tube was centrifuged by using a centrifugal separator to obtain plasma. Potassium ion concentration in the resulting plasma was measured by means of a flame photometer (Corning model 460). The results are shown in Table 1.

TABLE 1

| Present invention | Bemliese GS 303 (Asahi Kasei Industry Co., Ltd.) | 3.4 meq/l |
|---|---|---|
| Comparison | 100% polyester cloth | 3.4 |
| | medical bandage | 4.5 |
| | Rapia S (Teijin) | 4.0 |
| | no distributor | 3.4 |

It is apparent from Table 1 that when medical bandage and Rapia S are used, the extent of hemolysis is large, and that when Bemliese GS 303 and 100% polyester cloth are used, the extent of hemolysis is small. However, 100% polyester cloth has much difficulty in cutting it to give a member of an optinal form. Further, the 100% polyester cloth shows poor whole blood-spreadability, while when Bemliese GS 303 is used, the extent of hemolysis is small, it can be readily cut into a given size and whole blood spreads rapidly.

It was confirmed by a test comprising spotting a whole blood an absorbent material that a whole blood spreads in the Bemlinese GS 303 at a rate approx. 3 times as much as the rate in the 100% polyester cloth.

EXAMPLE 2

Measurement of potassium ion concentration

A pair of potassium ion-selective electrodes was incorporated into the ion activity measuring device of FIG. 1 disclosed in Japanese Patent Application No. 59(1984)-244199 at its central position, and each of distributing cloths given in the following table was used to prepare an ion activity measuring device for measuring plural kinds of ions. 50 μl of whole blood collected with heparin was used as liquid sample and 50 μl of Calibrate level-2 (potassium ion concentration: 4.9 meq/l, available from Warner-Lambert) was used as a reference liquid, One minute after spotting, a potential difference between a pair of the potassium ion-selective electrodes was measured to determine potassium ion concentration.

The result are shown in Table 2.

TABLE 2

| Present invention | Bemliese TS 507 (Asahi Kasei) | 3.8 meq/l |
|---|---|---|
| | Bemliese GS 204 (Asahi Kasei) | 3.9 |
| | Bemliese GS 303 (Asahi Kasei) | 4.0 |
| | Bemliese W 252 (Asahi Kasei) | 3.9 |
| Comparison | medical bandage | 4.6 |
| | plasma after centrifugation (flame photometer) | 3.9 |

It is clear from Table 2 that when nonwoven fabric composed of cellulosic long fibers according to the present invention is used, the measured value of potassium ion concentration in whole blood is nearly equal to that in plasma. This means that when the nonwoven fabric of the present invention is used, the extent of hemolysis is small.

EXAMPLE 3

Bemliese GS 303 was used as four sheets of liquid distributing members 36 of the ion activity measuring device shown in FIG. 3 to prepare an ion activity measuring device for measuring ion activity of plural kinds of ions. 50 μl of Calibrate level-2 (potassium ion concentration: 4.9 meq/l, available from Warner-Lambert) was used as a reference liquid. 50 μl of whole blood collected with heparin and 50 μl of plasma obtained after centrifugation of said whole blood were used as liquid samples. Potassium ion concentration in each of 100 liquid samples was measured and it was found that differences in the measured values of potassium ion concentration between whole blood and plasma were 0.5 meq/l at most.

EXAMPLE 4

(1) Preparation of Ag/AgCl electrode

On a polyethylene terephthalate (PET) film having thickness of 180 μm was evaporated a continuous silver layer of 8000 angstroms thick. The film was then cut to have width of 24 mm. The film was engraved to produce a groove (depth 70 μm) along the width direction at the center portion using an edge of a knife. Both ends were coated with a solution of polyvinyl chloride in a mixture of toluene and methyl ethyl ketone (resist for production of separatable mask film). The coated layers were dried to give protective layers of 30 μm thick. Thus treated film was immersed for 90 min. in an oxyhalogenating solution containing hydrochloric acid (60 mmol./l) and potassium bichromate (12 mmol./l at 30° C. The film was then washed with water and dried to give an Ag/AgCl electrode sheet.

(2) Preparation of sodium ion-selective electrode

A solution having the following composition was coated on the above-obtained Ag/AgCl electrode and dried.

Sodium chloride: 6 g
Water: 50 g
Ethanol: 40 g

On the dried layer was further coated a solution of the following composition to have thickness after dryness of 25 μm.

Vinyl chloride-vinyl acetate copolymer (polymerization ratio=90:10, VYNS, tradename of Union Carbide Corp.): 0.9 g
Dioctyl sebacate: 1.2 g
Methylmonensin: 0.1 g
Sodium tetraphenylborate: 0.002 g
Methyl ethyl ketone: 5.0 g
Surfactant (1% solution, SH-510 available from Shinetsu Chemical Industry, Co., Ltd., Japan): 0.06 g The resist layers coated on both ends of the film were removed to expose the silver metal surface, whereby forming electrically connecting terminals. The film was then cut to have width of 5 mm to prepare a sodium ion-selective electrode.

(3) Preparation of potassium ion-selective electrode

A solution having the following composition was coated on the above-obtained Ag/AgCl electrode and dried.

Sodium chloride: 2.78 g
Potassium chloride: 2.22 g
n-Propyl alcohol: 32 g
Water: 96 g Surfactant (1% solution, SH-510 available from Shi-netsu Chemical Industry, Co., Ltd., Japan): 0.06 g On the dried layer was further coated a solution of the following composition to have thickness after dryness of 30 μm.

Vinyl chloride-vinyl acetate copolymer (polymerization ratio=90:10, VYNS, tradename of Union Carbide Corp.): 0.9 g
Dioctyl phthalate: 2.4 g
Valinomycin: 44 mg
Potassium tetrakis-p-chlorophenylborate: 6 mg
Methyl ethyl ketone: 5.9 g
Surfactant (1% solution, SH-510 available from Shi-netsu Chemical Industry, Co., Ltd., Japan): 0.06 g The resist layers coated on both ends of the film were removed to expose the silver metal surface, whereby forming electrically connecting terminals. The film was then cut to have width of 5 mm to prepare a potassium ion-selective electrode.

(4) Preparation of chlorine ion-selective electrode

A solution having the following composition was coated to have thickness of 12 μm after dryness on the above-obtained Ag/AgCl electrode and dried.

Polyvinyl butyral 1.0 g
Trioctylmethylammonium chloride 1.0 g
Valinomycin 44 mg
Ethanol 7.0 g
Surfactant (1% solution, SH-510 available from Shi-netsu Chemical Industry, Co., Ltd., Japan) 0.04 g.

The resist layers coated on both ends of the film were removed to expose the silver metal surface, whereby forming electrically connecting terminals. The film was then cut to have width of 5 mm to prepare a chlorine ion-elective electrode.

(5) Assembly of ion activity-measuring device

Figure 4:
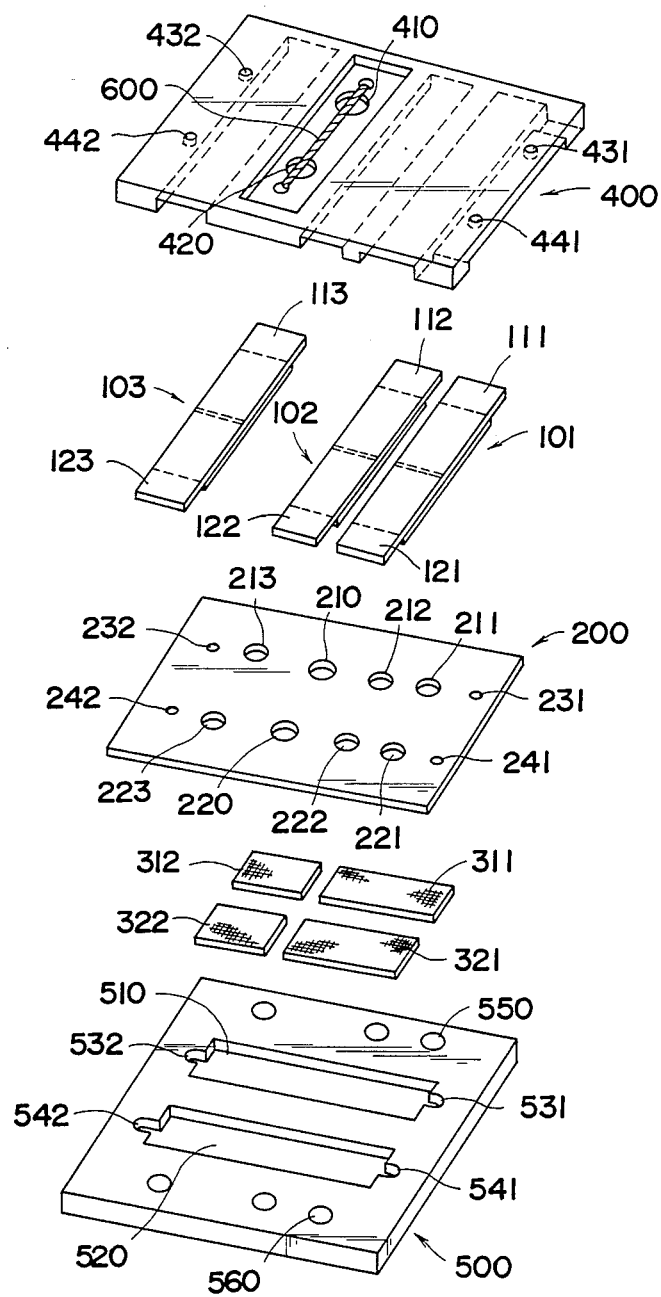
FIG. 4 shows members of still other embodiment of the ion activity measuring device of the invention.

In the grooves of plastic frame 400 (length 28 mm, width 24 mm) as illustrated in FIG. 4, which had a pair of liquid-spotting openings 410, 420 (diameter 4 mm) and two pairs of air-vents 431, 432 and 441, 442 were placed the sodium ion-selective electrode 103 on one side and the potassium ion-selective electrode 102 and the chlorine ion-selective electrode 101 on another side via the liquid-spotting openings 410, 420. The electrodes were arranged to expose their ion-selective layers. On the face of the electrodesand the frame was placed double-coated tape 200 having a pair of liquid-receiving openings 210, 220 and three pairs of liquid-supplying openings 213, 223, and 212, 222, and 211, 221, in such manner that each low of the liquid-supplying openings faced each of the face of the electrode.

The distance from the center of the liquid-receiving opening 210 to the center of the liquid-supplying openings 213, 212 and the distance from the center of the liquid-receiving opening 220 tothe center of the liquid-supplying openings 223, 222 were both 5.8 mm. The distance between the centers of the liquid-supplying openings, 212, 211 and the distance between the centers of the liquid-supplying openings 222, 221 were both 5. 7 mm.

A pair of liquid-distributing members (width 2 mm, length 13 mm, Bemliese GS 303, tradename of Asahi Kasei Co., Ltd., a nonwoven fabric of long cellulose fibers) 311, 321, and another pair of liquid-distributing members (width 2 mm. length 7.3 mm, same material) 312, 322 and were fixed on the double-coated tape 200 to position their one ends at 1 mm from the centers of the liquid-supplying openings 210, 220 and to cover the liquid-supplying openings. Onto thus arranged area, polyethylene support frame 500 having a pair of registration grooves 510, 520 was adhered in such manner that the grooves 510, 520 received therein the liquid-distributing members.

Thus prepared ion activity-measuring device was used in such manner that the liquid-spotting openings looked upward.

(7) Measurement of Electric Potential

In the liquid-spotting opening for a sample liquid of the above-prepared ion activity-measuring device was spotted 50 μl of a whole blood (which was collected in the presence of heparin), while in the liquid-spotting opening for a reference liquid was spotted a reference liquid having the following composition. The spottings were done simultaneously. The electric potential differences ocurring at one minute after the spotting were measured via the electrode terminals 113, 123, and 112, 122, and 111, 121, using Orion Microprocessor Model 901 (produced by Orion Corp.). For comparison, the same measurement of potential difference was done using a plasma obtained by centrifuging the same whole blood.

The results are set forth in Table 3, wherein the values are average values of potassium ion activity (or sodium ion activity, or chlorine ion activity) determined using five measured values each after one minute and a calibration curve.

TABLE 3

| Sample | Ion Activity (meq/l) | | |
|---|---|---|---|
| | K ion | Na ion | Cl ion |
| Whole blood | 4.0 | 140.1 | 103.9 |
| Plasma | 3.9 | 140.0 | 104.4 |

The results set forth in Table 3 clearly indicate that substantially no hemolysis took place in the ion activity-measuring device.

We claim:

1. In a device for measuring ion activity in a liquid sample comprising at least one pair of ion-selective electrodes selectively responsive to a specific ion, a porous liquid distributing member for feeding a liquid sample to one electrode of the pair of electrodes, a porous liquid distributing member for feeding a reference liquid to another electrode of the pair of electrodes and a porous bridge for electrically connecting both liquids to each other, the improvement wherein said liquid distributing members are made of a nonwoven fabric composed of cellulosic long fibers prepared from cotton linters.

2. The device for measuring ion activity as claimed in claim 1, wherein there are provided at least two pairs of ion-selective electrodes.

3. The device for measuring ion activity as claimed in claim 1, wherein said nonwoven fabric is one prepared from a spinning solution of cotton linters dissolved in Schweizer's reagent by a spun bonding method.

4. The device for measuring ion activity as claimed in claim 1, wherein said liquid distributing members are porous members which absorb blood in an amount of as at least 10 times by weight as much as that of said member for a period of 3 seconds.

* * * * *